United States Patent [19]

Mangold et al.

[11] 4,095,034

[45] June 13, 1978

[54] MANUFACTURE OF α-NAPHTHYL-N-METHYL-CARBAMATE

[75] Inventors: Dietrich Mangold, Neckargemuend; Karl-Heinz Koenig, Frankenthal; Christian Reitel, Heidelberg, all of Germany

[73] Assignee: BASF Aktiengesellschaft, Ludwigshafen am Rhein, Germany

[21] Appl. No.: 675,580

[22] Filed: Apr. 9, 1976

[30] Foreign Application Priority Data

May 2, 1975 Germany .............................. 2519584

[51] Int. Cl.$^2$ ........................................... C07C 125/06
[52] U.S. Cl. .................................... 560/134; 560/132; 560/157; 560/162; 560/164; 560/166
[58] Field of Search ....................... 260/479 C, 482 C; 560/134

[56] References Cited

FOREIGN PATENT DOCUMENTS 1,910,295 10/1969 Germany .......................... 260/479 C

*Primary Examiner*—Natalie Trousof
*Assistant Examiner*—Jane T. Fan
*Attorney, Agent, or Firm*—Keil, Thompson & Shurtleff

[57] ABSTRACT

Process for the manufacture of N-alkyl and N-alkenyl carbamates by reacting a hydroxyl compound with a carbamyl chloride essentially free from phosgene and hydrogen chloride at a temperature of from 60° to 130° C in alkyl or halogen benzenes as solvent.

3 Claims, No Drawings

MANUFACTURE OF α-NAPHTHYL-N-METHYL-CARBAMATE

The present invention relates to a process for the manufacture of N-alkyl and N-alkenyl carbamates by reacting a hydroxyl compound with alkyl and alkenyl carbamyl chlorides respectively.

N-alkyl and N-alkenyl carbamates are well known for their excellent biological activity. For example, N-methyl carbamates of phenols and naphthols (German Pat. No. 962,164; U.S. Pat. No. 2,903,478; German Pat. No. 1,138,277) are of considerable economic significance as insecticides.

The synthesis of carbamic esters by reacting a hydroxyl compound with a carbamyl chloride according to the equation

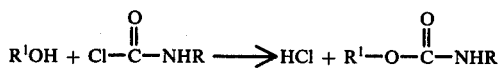

is well known. This method was first described in Ann. Chem., 244, 29, (1888), and was proposed as an analysis method for determining hydroxyl groups. The reaction takes place in the absence of hydrogen chloride acceptors.

German Pat. No. 1,468,496 describes a process for the manufacture of carbamic esters according to the above reaction. In this method, the reactants are placed in a low-boiling solvent (carbon tetrachloride) and reacted without the addition of hydrogen chloride acceptors at a temperature differing slightly from room temperature. The hydrogen chloride liberated during the reaction is entrained out of the system by means of an inert gas or by distilling off one of the reactants present in excess.

On completion of the reaction the solvent is removed and the carbamate isolated. Low reaction temperatures mean long reaction times, which are not less than 15 hours in the Examples given.

German Laid-Open Application No. 1,910,295 relates to a process for the manufacture of α-naphthyl-N-alkyl-carbamates, in which carbamyl chlorides obtained by gas-phase phosgenation of amines (JACS, 72, 1888 (1950)) are stirred into a solution of α-naphthol heated at from 30° to 130° C. The solvents recommended are high-boiling ligroins or mixtures of aromatic and aliphatic compounds. The excess of phosgene required for gas-phase phosgenation is fed to the reaction solution together with the carbamyl chloride formed and hydrogen chloride. This necessarily leads to solutions having a high content of phosgene, which are difficult to handle on an industrial scale and necessitate special safety precautions.

In the process of the invention for the manufacture of carbamates of the general formula I $$R^1-NH-COOR^2 \qquad I,$$

in which $R^1$ denotes straight-chain or branched-chain alkyl or alkenyl of up to 4 carbon atoms and $R^2$ denotes unsubstituted phenyl or naphthyl; phenyl or naphthyl mono- or poly-substituted by alkyl, alkoxy or halogen; straight-chain or branched-chain alkyl optionally interrupted by oxygen or optionally substituted by alkoxy or phenoxy; straight-chain or branched-chain alkenyl; cycloalkyl; or a radical of the formula $R^3OOCNHR^1$, where $R^1$ has the meaning given above and $R^3$ denotes divalent straight-chain or branched-chain alkyl optionally interrupted by oxygen, by the reaction of carbamyl chlorides with hydroxyl compounds, a carbamyl chloride which is essentially free from phosgene and hydrogen chloride and has the general formula II $$R^1NHCOCl \qquad II,$$

where $R^1$ has the meaning stated above, is reacted in the absence of acid-binding agent with a hydroxyl compound of the general formula III $$R^2OH \qquad III,$$

where $R^2$ denotes unsubstituted phenyl or naphthyl; phenyl or naphthyl mono- or poly-substituted by alkyl, alkoxy or halogen; straight-chain or branched-chain alkyl optionally interrupted by oxygen and optionally substituted by alkoxy or phenoxy; straight-chain or branched-chain alkenyl; cycloalkyl; or a radical of the formula $R^3OH$, where $R^3$ has the meaning stated above, at a temperature near the temperature of decomposition of the carbamyl chloride, in mono- or poly-substituted alkyl- or halo-benzenes as solvent.

The advantages of the process of the invention are that it involves short reaction times, gives high yields and causes no environmental problems. The carbamic esters produced by the invention are obtained in a very pure form and can be used without additional purification. The reaction times required are in the range of only a few minutes. The reaction proceeds without acid-binding agents.

Preferred starting materials are carbamyl chlorides such as are obtained by gas-phase phosgenation of amines according to JACS, 72, 1888, (1950).

In contrast to the teaching given in German Laid-Open Application 1,910,295, the phosgene excess required in the phosgenation of the amines (from 10 to 30% molar) is removed from the carbamyl chloride together with hydrogen chloride formed and is destroyed in a scrubbing tower or, if desired, recycled after removal of the hydrogen chloride. The carbamyl chloride used has a phosgene content of less than 0.1% by weight and a hydrogen chloride content of less than 0.1% by weight.

This avoids the occurrence of phosgene-containing solvents. It also excludes side reactions and thus losses of yield. If an excess of phosgene were introduced into the solution of the hydroxyl compound, particularly at elevated temperatures, chlorocarbonic esters would be formed which could react further with carbamyl chlorides possessing a free proton at the nitrogen atom to form allophanyl chlorides.

It is particularly advantageous to carry out the process at temperatures ranging from 60° to 130° C, preferably from 70° to 90° C.

The hydrogen chloride formed during synthesis of isocyanate or in the direct reaction of carbamyl chloride with the hydroxyl component is conveniently removed from the reaction as it proceeds. For example, it may be entrained from the reaction solution by means of an inert gas, preferably nitrogen, and then passed to a scrubbing tower together with the mixture of phosgene and hydrogen chloride from the phosgenation reaction for the synthesis of the carbamyl chloride. After removal of phosgene it may be absorbed in water to form hydrochloric acid.

The purity of the final product depends on reaction medium employed. Suitable solvents are benzenes mono-substituted or poly-substituted by alkyl or halogen and preferably having a boiling point above the reaction temperature to avoid the entrainment of undue amounts of solvent vapors with the liberated hydrogen chloride and any inert gas used, which would hamper working-up of said hydrogen chloride. Suitable solvents are aromatic hydrocarbons, for example toluene, o-xylene, m-xylene, p-xylene, ethylbenzene, n-propylbenzene, cumene, pseudocumene, t-butylbenzene, p-cumene, n-butylbenzene, 1,3,5-triethylbenzene, tetraline, chlorobenzene, o-dichlorobenzene and p-dichlorobenzene. Preferred solvents are the alkyl benzenes, particularly cumene.

Cumene has been found to be an optimum solvent, particularly for the synthesis of α-naphthyl-N-methylcarbamate used commercially as an insecticide. Since the commercial α-naphthol used for the synthesis always contains β-naphthol as impurity, synthesis of the carbamate also results in the formation of β-naphthyl-N-methylcarbamate as a byproduct, which has no insecticidal action and therefore reduces the biological activity of the insecticide. If the starting concentration of naphthol in the cumene is from 20 to 40% by weight, based on cumene, the cumene will keep the β-naphthyl-N-methylcarbamate in solution when the reaction mixture is cooled, whilst the α-naphthyl carbamate is precipitated as a pure crystalline solid.

Cumene is also particularly suitable as a solvent in the synthesis of other carbamates. Even when reaction mixtures of higher concentrations are used, the carbamate formed remains completely dissolved at the reaction temperature. When the reaction mixture is cooled to temperatures between 0° C and room temperature, the carbamate precipitates as a readily filtrable solid requiring no further purification.

Suitable starting compounds are alkyl- or alkenyl-carbamyl chlorides of up to 4 carbon atoms in the straight-chain or branched-chain alkyl or alkenyl radical, for example methyl, ethyl, n-propyl, isopropyl, n-butyl, t-butyl, vinyl, allyl and isopropenyl carbamyl chlorides.

Suitable hydroxyl compounds are straight-chain or branched-chain, unsubstituted or alkoxy- or phenoxy-substituted alkanols, alkane diols or cyclic alcohols, for example n-propanol, isobutanol, neopentyl alcohol, cyclohexanol, 3-methylbuten-2-ol-1, 2-phenoxyethanol and diethylene glycol, or unsubstituted phenols or naphthols, or phenols or naphthols mono- or poly-substituted by alkyl, alkoxy or halogen, for example phenol, o-cresol, m-cresol, p-cresol, xylenols, 3,4-dimethylphenol, 3,5-diethylphenol, 3-isopropyl-5-methylphenol, 4-isopropylphenol, carvacrol, thymol, 3,5-di-t-butylphenol, guaiacol, 2-isopropoxyphenol, o-chlorophenol, α-naphthol and β-naphthol.

The concentration of the hydroxyl component in the solvent may be varied within wide limits. It is advantageously between 10 and 50% by weight and preferably between 20 and 40% by weight, based on the solvent.

In a preferred embodiment of the process, 0.5 mole of β-naphthol is dissolved in sufficient solvent to form an approximately 20–40% w/w solution, based on solvent. At a temperature ranging from 70° to 120° C the carbamyl chloride obtained in the gas-phase phosgenation of an amine and essentially free from phosgene and hydrogen chloride is passed into the solution at the same rate as that at which it is formed. Inert gas, for example nitrogen, simultaneously bubbled through the reaction solution removes the hydrogen chloride liberated during the reaction. Said hydrogen chloride is then passed through a scrubbing tower together with the phosgene/hydrogen chloride mixture from the phosgenation stage. The reaction is over after a few minutes. The hot solution is cooled and the precipitated carbamate is filtered off.

For the purpose of identifying the carbamates, the melting points (with decomposition) are stated. Further identification of the products is provided by IR and NMR spectroscopic data, thin-layer chromatography and ultimate analysis.

EXAMPLE 1

Preparation of β-naphthyl-N-methylcarbamate 72 parts by weight of β-naphthol are dissolved in 250 parts by weight of t-butylbenzene at 80° C. 46.7 parts by weight of methylcarbamyl chloride are passed into this solution over a period of 10 minutes while nitrogen is simultaneously bubbled through the solution. The reaction is complete after 15 minutes. The hot reaction solution is then cooled to 0° C. 83.5 parts by weight of β-naphthyl-N-methylcarbamate are precipitated, this being equivalent to a yield of 83% of theory. The melting point is 119° C.

EXAMPLE 2

Preparation of 3,5-diethylphenyl-N-methylcarbamate 75 parts by weight of 3,5-diethylphenol are dissolved in 250 parts by weight of o-xylene at 80° C. 46.7 parts by weight of methylcarbamyl chloride are fed into this solution over a period of 10 minutes while nitrogen is simultaneously bubbled through the solution. The reaction is complete after about 20 minutes. Cooling of the hot reaction solution to 0° C causes precipitation of 8 parts by weight of 3,5-diethylphenyl-N-methylcarbamate, equivalent to a yield of 85% of theory; m.p. 101° C.

EXAMPLE 3

Preparation of β-naphthyl-N-methylcarbamate 72 parts by weight of β-naphthol are dissolved in 250 parts by weight of cumene at 80° C. 46.7 parts by weight of methylcarbamyl chloride are stirred into this solution over a period of 10 minutes while nitrogen is simultaneously bubbled through the solution. The reaction is complete after 15 minutes. The hot reaction solution is cooled to 0° C and the precipitated β-naphthyl-N-methylcarbamate is isolated. The yield is 85% of theory.

In the same manner, the carbamates listed in the Table below were synthesized. The yields given in percent by weight, based on hydroxyl compound used, relate to the amount of carbamate isolated on cooling the reaction solution to 0° C.

| Carbamic ester | Yield (% w/w) | m.p. (° C) |
| --- | --- | --- |
| naphthalen-1-yl O-C(=O)-NHCH₃ | 85 | 139-141 |
| naphthalen-2-yl O-C(=O)-NHCH₃ | 85 | 119 |
| naphthalen-2-yl O-C(=O)-NH-CH(CH₃)₂ | 92 | 129 |
| naphthalen-2-yl O-C(=O)-NH-CH₂-CH=CH₂ | 95 | 123 |
| naphthalen-2-yl O-C(=O)-NH-CH₂-CH₂-CH₃ | 95 | 140 |
| naphthalen-2-yl O-C(=O)-NH-(CH₂)₃-CH₃ | 95 | 121 |
| 3,5-diethylphenyl O-C(=O)-NH-CH₃ | 92 | 101 |
| phenyl-O-CH₂-CH₂-O-C(=O)-NHCH₃ | 100 | 93 |
| 4-methylphenyl O-C(=O)-NH-CH₃ | 92 | 94 |
| (CH₃NH-C(=O)-O-CH₂-CH₂)₂O | 93 | 92 |

We claim:

1. A process for the manufacture of α-naphthyl-N-methylcarbamate by the reaction of methylcarbamyl chloride and α-naphthol containing β-naphthol as an impurity, which comprises reacting methylcarbamyl chloride, which is essentially free from phosgene and hydrogen chloride, in the absence of an acid-binding agent, with α-naphthol containing β-naphthol as an impurity at a temperature in the range of 60° to 130° C in, as solvent, cumene, the starting concentration of said naphthol in the cumene being in the range of 20 to 40% by weight, based on the cumene, and cooling the reaction mixture to precipitate the α-naphthyl-N-methylcarbamate as a pure crystalline solid, the β-naphthyl-N-methylcarbamate formed in the reaction remaining in solution in the cumene when the reaction mixture is cooled.

2. A process as claimed in claim 1, wherein the hydrogen chloride formed during the reaction is entrained from the reaction solution by an inert gas.

3. A process as claimed in claim 1, wherein the reaction is carried out at a temperature ranging from 70° to 90° C.

* * * * *